United States Patent [19]

Wilson et al.

[11] Patent Number: 4,988,509

[45] **Date of Patent: * Jan. 29, 1991**

[54] USE OF DIBUTYL SUCCINATE AS INSECT ATTRACTANT

[75] Inventors: Richard A. Wilson, Westfield, N.J.; Jerry F. Butler, Gainesville, Fla.; Donald A. Withycombe, Lincroft, N.J.; Braja D. Mookherjee, Holmdel, N.J.; Ira Katz, West Long Branch, N.J.; Kenneth R. Schrankel, Tinton Falls, N.J.

[73] Assignees: International Flavors & Fragrances Inc., New York, N.Y.; The University of Florida, Gainesville, Fla.

[ * ] Notice: The portion of the term of this patent subsequent to Apr. 4, 2006 has been disclaimed.

[21] Appl. No.: 930,419

[22] Filed: Nov. 14, 1986

Related U.S. Application Data

[63] Continuation-in-part of Ser. No. 879,351, Jun. 27, 1986, Pat. No. 4,801,448.

[51] Int. Cl.$^5$ ............................................. A01N 25/00
[52] U.S. Cl. ......................................... 424/84; 424/78
[58] Field of Search .................................... 424/84, 78

[56] References Cited

U.S. PATENT DOCUMENTS 4,600,581 7/1986 Aldrich ................................ 424/84

*Primary Examiner*—Allen J. Robinson
*Attorney, Agent, or Firm*—Arthur L. Liberman

[57] ABSTRACT

Described are the uses of alpha-terpineol having the structure:

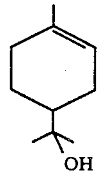

and dibutyl succinate having the structure:

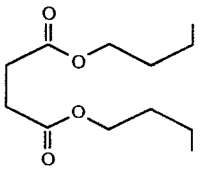

taken alone or in combination as attractants for female Mediterranean sand flies (*Phlebotomus papatasi*).

The dubutyl succinate and alpha-terpineol taken alone or in combination find utility primarily as bait enhancers for acute toxins and/or trapping devices.

1 Claim, 3 Drawing Sheets

USE OF DIBUTYL SUCCINATE AS INSECT ATTRACTANT

This application is a continuation-in-part of application for U.S. Letters Patent, Ser. No. 879,351 filed on June 27, 1986, now U.S. Pat. No. 4,801,448.

BACKGROUND OF THE INVENTION

This invention relates to attractants for a species of sand fly (*Phlebotomus papatasi*). More particularly, this invention relates to compositions of matter containing alpha-terpineol or dibutyl succinate or combinations of alpha-terpineol and dibutyl succinate as attractants for *Phlebotomus papatasi.*

The *Phlebotomus papatasi* species is a well known vector for leishmaniasis, a group of conditions caused by the Leishmann species of Protozoa as stated in the Merck Manual (Published by Merck & Co., Rahway, N.J. 1956) at page 985. Depending on the strain of Leishmania causing it leishmaniasis may manifest itself as "Kala-azar" (*L. donovani*), "Oriental sore" (*L. tropica*), or "American leishmaniasis" (*L. braziliensis*).

Furthermore, fast intercontinental travel and trade are stepping up chances of importing nonindigenous insect pests into the U.S. Attractants, or lures, can be of considerble aid in facilitating the early detection of such insect pests, and they are of vital importance in measuring the progress of a program aimed at eradicating a species that has become established.

In Agriculture Handbook No. 239 published by the Agricultural Research Service of the U.S. of America Department of Agriculture issued in June 1963 entitled, "Materials Tested As Insect Attractants", compiled by M. Beroza and N. Green, "terpineol" is indicated to have a good attractancy index ("2" on a scale of 1 to 3 for the Oriental Fruit Fly and "1" on a scale of 1 to 3 for the Mediterranean Fruit Fly, the Melon Fly and the Mexican Fruit Fly.

The dibutyl ester of succinic acid is indicated in Agriculture Handbook No. 239 to attract the Oriental Fruit Fly only slightly ("1" on a scale of 1 to 3) whereas the dibutyl ester of 1,1,3,5-tetramethyl-2-octenyl succinic acid is indicated to attract the Oriental Fruit Fly at a level of "2" on a scale of 1 to 3; the Melon Fly at a level of "1" on a scale of 1 to 3; the Mediterranean Fruit Fly at a level of "1" on a scale of 1 to 3; and the Mexican Fruit Fly at a level of "1" on a scale of 1 to 3. The dibutyl ester of tartaric acid is indicated to attract the Oriental Fruit Fly at a level of "2" on a scale of 1 to 3; it is indicated to attract the Melon Fly at a level of "1" on a scale of 1 to 3; and it is indicated to attract the Mediterranean Fruit Fly at a level of "2" on a scale of 1 to 3.

On the other hand, di-n-butyl succinate having the structure:

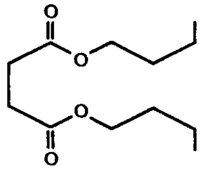

is indicated as a fly repellent in U.S. Letters Patent 2,991,219 issued on July 4, 1961. In addition, the insect repellency properties of di-n-butyl succinate is disclosed in U.S. Letters Patent No. 2,937,969 issued on May 24, 1960 and in U.S. Letters Patent No. 2,971,881 issued on Feb. 14, 1961.

However, nothing in the prior art discloses the use of either alpha-terpineol having the structure:

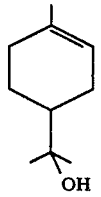

or di-n-butyl succinate having the structure:

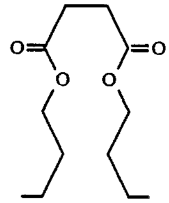

or combinations thereof in attracting the (*Phlebotomus papatasi*) species of the sand fly.

SUMMARY OF THE INVENTION

Figure 1:
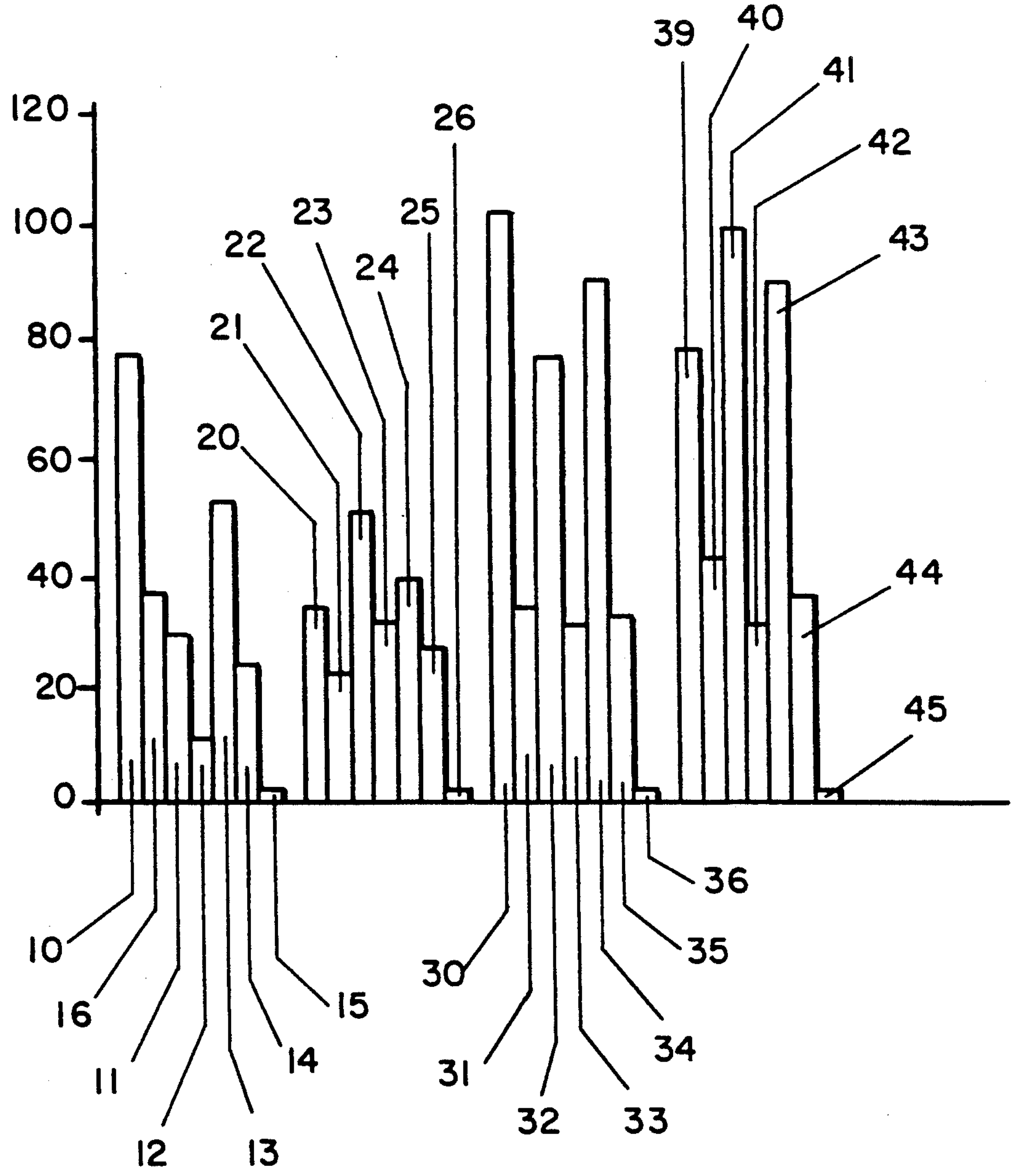
FIG. 1 is a bar graph showing a comparsion of the field trial tests of attractants for male and female (*Phlebotomus papatasi*) comparing dibutyl succinate, alpha-terpineol and a control which does not contain any additives (a "blank"), the graph being compound or "blank" versus (*Phlebotomus papatasi*)/trap.

Our invention relates to the use of dibutyl succinate, alpha-terpineol or combinations thereof as attractants for female Mediterranean sand flies (*Phlebotomus papatasi*).

The trapping system used for testing the efficacy of the alpha-terpineol and dibutyl succinate and combinations thereof is a standard "CDC" (Communicable Disease Center) trap as published in Mosquito News, Volume 30, No. 1, at page 20 (Fay and Prince, "A Modified Visual Trap For *Aedes Aeqypti*)(Source: Biology Section, Technical Development Laboratories, Laboratory Division, National Communicable Disease Center, Health Services and Mental Health Administration, Public Health Service, U.S. Department of Health, Education, and Welfare, Savannah, Ga. 31402). The trap is set forth in detail in the "Detailed Description of The Drawings" section, infra. The design is based on the attraction of contrasting gloss black and white panels and involves a wind-orienting cover, a stationary cylinder housing the suction motor, and a cage to hold the trapped sand flies. Such "CDC" traps are marketed by Housherr's Machine Works, Old Freehold Road, Toms River, N. J. 08753 and the John W. Hock Company, P.O. Box 12852, Gainesville, Fla. 32604.

Our invention also relates to the formation of female Mediterranean sand fly (*Phlebotomus papatasi*) attractant-containing polymeric pellets by means of introduction into a single screw or twin screw extruder of, in series, thermoplastic polymer followed by the female Mediterranean sand fly (*Phlebotomus papatasi*) attractant which is compatible with the thermoplastic polymer, in turn, followed by introduction of a gaseous blowing agent or blowing agent which will produce a gas which is inert to the polymer and to the female Mediterranean sand fly (*Phlebotomus papatasi*) attractant, e.g., dibutyl succinate or alpha-terpineol. In the alternative, the use of the foaming agent can be omitted.

The nature of the extruder utilized in this aspect of our invention to form the polymeric female Mediterranean sand fly (*Phlebotomus papatasi*) attractant particles of our invention may be either single screw or double screw. Thus, the types of extruder that can be used are disclosed at pages 246–267 and 332–349 of the clopedia, 1982–1983 published by the McGraw-Hill Publishing Company, the disclosure of which is incorporated by reference herein. More specifically, examples of extruders which are useable in carrying out this aspect of our invention (with modification for introduction of the female Mediterranean sand fly (*Phlebotomus papatasi*) attractant downstream from introduction of the polymer and optionally with a further modification that the gaseous blowing agent is introduced still further downstream from the point of introduction of insect attractant) are as follows:

1. The Welex "Super Twinch" 3.5" extruder manufactured by Welex Incorporated, 850 Jolly Road, Blue Bell, Pa. 19422;
2Krauss-Maffei twin screw extruder manufactured by the Krauss-Maffei Corporation/Extruder Division, 3629 West 30th Street South, Wichita, Kans. 67277;
3. Modified Sterling Model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the Americal Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 048601; and
9. The Berstorff single screw, twin screw, or foam extrusion equiptment manufactured by Berstorff Corporation, P.O. Box 240357, 8200-A Arrowridge Boulevard, Charlotte, N.C. 28224.

In producing the female Mediterranean sand fly (*Phlebotomus papatasi*) attractant-containing polymer particles of our invention, various polymers may be utilized, for example, low density polyethylene, high density polyethylene, polypropylene, the co- polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate; and (e) acrylic acid including the hydrolyzed co-polymers of ethylene and vinyl acetate. Preferred co-polymers are ethylene vinyl acetate with about 9 to 60% vinyl acetate and ethylene/ethyl acrylate with about 6to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX®" and by the Arco Polymer Division under the trademark "DYLAND®" and by the Exxo of Linden, N.J. under the trademark "DEXXON®. Ethylene/ethyl acrylate copolymers are marketed by Union Carbide Corporation under the tradename "EEA RESINS®".

The polymer is added to the single screw or twin screw extruder at a feed rate in the range of from about 80 up to about 300 pounds per hour while maintaining the temperature in the screw extruder between about 160° C. and about 240° C. If the polymer or co-polymer powder is added to the extruder at a reference "barrel segment", then the female Mediterranean sand fly (*Phlebotomus papatasi*) attractant is added to the extruder under pressure down-stream from the addition point of the polymer at 1 or more "barrel segments" S-2, S-3, S-4, S-5, S-6, S-7, S-8or S-9.

Thus, the invention provides a process for forming the female Mediterranean sand fly (*Phlebotomus papatasi*) attractant-containing polymeric particles such as polymeric pellets which include a relatively high concentration of the female Mediterranean sand fly (*Phlebotomus papatasi*) attractant added at "barrel segments" S-2, S-3, S-4, S-5, S-6, S-7, S-8 or S-9 of the single screw or twin screw extruder is to be compatible with the polymer added at barrel segment" S-1 of the single screw or twin screw extruder.

The proportion of the female Mediterranean sand fly (*Phlebotomus papatasi*) attractant is limited only by either (a) its solubility in the resin or mixture of resins used and/or (b) the volume ratio of microvoids in the polymer to said polymer and/or (c) the solubility of the female Mediterranean sand fly (*Phlebotomus papatasi*) attractant in the polymer on solidification. The proportion of the female Mediterranean sand fly (*Phlebotomus papatasi*) attractant can in many instances go up to 45% by weight or even higher.

Thus, the proportion of the female Mediterranean sand fly (*Phlebotomus papatasi*) attractant to resin can vary from small but effective amounts on the order of about 1% of the weight of the resin body up to about 45% by weight of the resin body. In general, it is preferred to use between about 5% up to about 30% based on the weight of resin body of the female Mediterranean sand fly (*Phlebotomus papatasi*) attractant. This is an optimum amount balancing the proportion of Mediterranean sand fly (*Phlebotomus papatasi*) attractant against the time period over which the article emits the female Mediterranean sand fly (*Phlebotomus papatasi*) attractant and against the tendency of the female Mediterranean sand fly (*Phlebotomus papatasi*) attractant to "oil out". This "oiling out" is specifically avoided as a result of the use of foaming agent.

As stated, supra, various polymers are useful in the practice of our invention. Specific examples of polymers useful in the practice of our invention are as follows:

(a) DYLAN ® brand of low density polyethylene DYLAN ® is a trademark owned by the Atlantic Richfield Company of Los Angeles, California;

(b) DYLITE ® of expandable polystryene compositions. DYLAN ® is a trademark of the Atlantic Richfield Company of Los Angeles, California;

(c) SUPER DYLAN ® a high density polyethylene. SUPER DYLAN ® is a trademark of the Atlantic Richfield Company of Los Angeles, California;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/alpha-olefin as exemplified and disclosed in U.S. Pat. No. 4,369,291, the specification for which is incorporated by reference herein;

(g) Poly-alpha-olefin as exemplified in Canadian Letters Patent No. 1,137,069 issued on Dec. 7, 1982, the specification for which is incorporated by reference herein;

(h) Polymeric compositions as disclosed in Canadian Letters Patent No. 1,137,068 issued on Dec. 7, 1982, the specification for which is incorporated by reference herein;

(I) Poly-alpha-olefins disclosed in Canadian Letters Patent No. 1,137,067, the specification for which is incorporated by reference herein;

(j) Polyolefins described in Canadian Letters Patent No. 1,137,066, the specification for which is incorporated by reference herein;

(k) Polyethylene oxides as disclosed in Canadian Letters Patent No. 1,137,065 issued on Dec. 7, 1982, the specification for which is incorporated by reference herein;

(l) Olefin polymers and co-polymers as disclosed in Canadian Letters Patent No. 1,139,737, the specification for which is incorporated by reference herein Canadian Patent No. 1,139,737 was issued on Jan. 18, 1983;

(m) Polyolefins disclosed in Canadian Letters Patent No. 1,139,738, the disclosure of which is incorporated by reference herein. Canadian Patent No. 1,139,738 was issued on Jan. 18, 1983;

(n) Chlorinated PVC as disclosed in *Polymer* 1982, 23 (7, Suppl.), 1051–6 abstracted at Chem.Abstracts 97:145570y, 1982;

(o) Polyepsilon caprolactone co-polymers made by means of alcohol initiated polymerization as disclosed in *J.Polym.Sci.* Polym. Chem. Ed. 1982, 20(2), pages 319-26, abstracted at Chem.Abstracts, Volume 96:123625x, 1982;

(p) Styrene acrylonitrile co-polymers as disclosed in Diss. Abstracts, Int. B, 1982, 42(8), 3346 and abstracted at Chem.Abstracts 96:143750n (1982);

(q) Co-polymers of epsilon caprolactone with 1,4-butane diol as disclosed at Kauch. Rezine, 1982, (2), 8-9, abstracted at Chem.Abstracts, Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al, *J.Polym.Sci.* Polym. Phys. Ed. 1982, 20(2), 191-203;

(t) Plasticized polyepsilon caprolactone co-polymers containing dimethyl phthalate plasticizers as set forth in Japanese Patent J81/147844, abstracted at Chem.Abstracts, Volume 96:69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,256,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Optionally, downstream from the addition point of the female Mediterranean sand fly (*Phlebotomus papatasi*) attractant a gaseous or liquid containing blowing agent may be added (e.g., at barrel segments S-5, S-6, S-7, S-8 or S-9 and S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed female Mediterranean sand fly (*Phlebotomus papatasi*) attractant-containing polymer particle.

The feed rate range of the female Mediterranean sand fly (*Phlebotomus papatasi*) attractant may be between about 0.5% up to about 45% by weight of the polymer.

The die of the extruder may create rod, sheet, film or ribbon. The resulting product may then, if desired, be pelletized to form foamed female Mediterranean sand flies (*Phlebotomus papatasi*) attractant-containing polymer particles or the ribbon may be used "as-is" as the female Mediterranean sand fly (*Phlebotomus papatasi*) attractant-containing polymeric article of manufacture itself.

In addition to the optional gaseous blowing agents (which are necessarily "inert" gases), blowing agents may be added at some point on the extruder which will create gaseous voids in the female Mediterranean sand fly (*Phlebotomus papatasi*) attractant-containing polymeric articles of our invention and these "blowing agents" are well known to one having ordinary skill in the art. Examples of such non-gaseous containing materials which yield gases on admixture with the polymer in the extruder but which are still inert to the female Mediterranean sand fly (*Phlebotomus papatasi*) attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CHCl_3$, $CF_2Cl_2$, $CH_3Cl$, $CH_2Cl_2$ separately or in admixture with one another as set forth in U.S. Pat. No. 3,758,425, column 4, lines 1-5, the-specification for which is incorporated by reference herein;

(iii) Diochlorotetrafluoroethane, tetramethylmethane, monochlorodifluoromethane, dichlorodifluoromethane, and dichlorotetrafluoroethane as specifically described in U.S. Pat. Nos. 2,948,644 and 2,948,665 issued on Aug. 9, 1960, the specification for which is incorporated by reference herein; and (iv) Azo bis(formamide); diazoaminobenzene; N,N'-diniotrosopentamethylene tetramine; N,N'-dimethyl-N,N'-dinitrosoterephthalamide; p,p'-oxy-bis(benzene sulfonyl semicarbazide); azo bis(isobutyronitrile); p,p'-oxy-bis(benzene sulfonyl hydrazide); p,p'-diphenyl-bis(-sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

FIG. 1 sets forth field trial tests for the attractants alpha-terpineol and dibutyl succinate as well as for dimethyl disulfide and "a blank" control insofar as their attractancy for Mediterranean sand flies (*Phlebotomus papatasi*) is concerned. FIG. 1 is a bar graph. The bars indicated by reference numerals 10, 11, 12, 13, 14, 15 and 16 are the bar graphs for the "blank" not containing any additive. The bar graphs indicated by reference numerals 20, 21, 22, 23, 24, 25 and 26 are the bar graphs for the comparative attractancy of male and female (*Phlebotomus papatasi*) of dimethyl disulfide. The bar graphs indicated by reference numerals 30, 31, 32, 33, 34, 35 and 36 are the bar graphs indicating the attractancy of male and female (*Phlebotomus papatasi*) using dibutyl succinate. The bar graphs indicated by reference numerals 39, 40, 41, 42, 43, 44 and 45 are the bar graphs showing attractancy of male and female (*Phlebotomus papatasi*) using alpha-terpineol. All of the data set forth in each of the bar graphs of FIG. 1 is obtained using a "CDC" (Communicable Disease Center) trap as set forth in detail, infra, and as set forth in FIG. 2 which is described in detail, infra.

The bar graph indicated by reference numeral 10 is the bar graph for the first replicate for female (*Phlebotomus papatasi*) using a "blank". The bar graph indicated by reference numeral 16 is the bar graph for the first replicate for male (*Phlebotomus papatasi*) using a "blank". The bar graph indicated by reference numeral 11 is the bar graph for the second replicate for female (*Phlebotomus papatasi*) using a "blank". The bar graph indicated by reference numeral 12 is the bar graph for the second replicate for male (*Phlebotomus papatasi*) using a "blank". The bar graph indicated by reference numeral 13 is the bar graph for the mean of replicates one and two for females. The bar graph indicated by reference numeral 14 is the bar graph for the mean of the two replicates for male (*Phlebotomus papatasi*). The bar graph indicated by reference numeral 15 is the bar graph indicating the ratio of female (*Phlebotomus papatasi*) to male (*Phlebotomus papatasi*) as attracted using a "blank".

The bar graph indicated by reference numeral 20 is the bar graph for the first replicate for female (*Phlebotomus papatasi*) using dimethyl disulfide. The bar graph indicated by reference numeral 21 is the bar graph for the first replicate for male (*Phlebotomus papatasi*) using as an attractant dimethyl disulfide.

The bar graph indicated by reference numeral 22 is the bar graph for the second replicate for attracting female (*Phlebotomus papatasi*) using as an attractant dimethyl disulfide. The bar graph indicated by reference numeral 23 is the bar graph for the second replicate for male (*Phlebotomus papatasi*) using as an attractant dimethyl disulfide. The bar graph indicated by reference numeral 24 is the bar graph showing the mean of the first replicate and the second replicate for female (*Phlebotomus papatasi*) using as an attractant dimethyl disulfide. The bar graph indicated by reference numeral 25 is the bar graph for the mean of replicate one and replicate two for male (*Phlebotomus papatasi*) using as an attractant dimethyl disulfide. The bar graph indicated by reference numeral 26 is the bar graph for the ratio of the mean of the replicates for females and the mean of the replicates for male (*Phlebotomus papatasi*) using as an attractant dimethyl disulfide.

The bar graph indicated by reference numeral 30 is the bar graph for the first replicate for female (*Phlebotomus papatasi*) using as an attractant dibutyl succinate. The bar graph indicated by reference numeral 31 is the bar graph for the first replicate for male (*Phlebotomus papatasi*) using as an attractant dibutyl succinate. The bar graph indicated by reference numeral 32 is the bar graph for the second replicate for female (*Phlebotomus papatasi*) using as an attractant dibutyl succinate. The bar graph indicated by reference numeral 33 is the bar graph for the second replicate for male (*Phlebotomus papatasi*) using as an attractant dibutyl succinate. The bar graph indicated by reference numeral 34 is the bar graph for the mean of the first replicate and the second replicate for attracting female (*Phlebotomus papatasi*) using as an attractant dibutyl succinate. The bar graph indicated by reference numeral 35 is the bar graph for the mean of replicate one and replicate two for male (*Phlebotomus papatasi*) using as an attractant dibutyl succinate. The bar graph indicated by reference numeral 36 is the bar graph for the ratio of attractancy for female (*Phlebotomus papatasi*)/male (*Phlebotomus papatasi*) using as an attractant dibutyl succinate.

The bar graph indicated by reference numeral 39 is the bar graph for the first replicate for female (*Phlebotomus papatasi*) using as an attractant alpha-terpineol. The bar graph indicated by reference numeral 40 is the bar graph for the first replicate for male (*Phlebotomus papatasi*) using as an attractant alpha-terpineol. The bar graph indicated by reference numeral 41 is the bar graph for the second replicate for female (*Phlebotomus papatasi*) using as an attractant alpha-terpineol. The bar graph indicated by reference numeral 42 is the bar graph for the second replicate for male (*Phlebotomus papatasi*) using as an attractant alpha-terpineol. The bar graph indicated by reference numeral 43 is the bar graph for the mean of the first replicate and the second replicate for female (*Phlebotomus papatasi*) using as an attractant alpha-terpineol. The bar graph indicated by reference numeral 44 is the bar graph for the mean for the second replicate and for the first replicate for male (*Phlebotomus papatasi*) using as an attractant alpha-terpineol. The bar graph indicated by reference numeral 45 is the bar graph for the ratio for attractancy of female (*Phlebotomus papatasi*)/male (*Phlebotomus papatasi*) using as an attractant alpha-terpineol.

The data supporting the bar graphs of FIG. 1 as described, supra, are set forth as follows:

TABLE I

| Treatment Composition | First Replicate: Female | First Replicate: Male | Second Replicate: Female | Second Replicate: Male | Mean Female | Mean Male | Ratio Female/Male |
| --- | --- | --- | --- | --- | --- | --- | --- |
| "Blank" | 78 | 38 | 31 | 11 | 54.0 | 24.5 | 2.20 |
| Dimethyl Disulfide | 36 | 23 | 51 | 32 | 40.5 | 27.5 | 1.47 |
| Dibutyl succinate | 103 | 36 | 78 | 32 | 90.5 | 34.0 | 2.66 |
| Alpha-terpineol | 80 | 44 | 101 | 32 | 90.5 | 38.0 | 2.38 |

The foregoing data gives rise to the conclusion from a statistical standpoint that alpha-terpineol and dibutyl succinate taken alone or in combination are attractants for the female Mediterranean sand fly (*Phlebotomus papatasi*).

Figure 2:
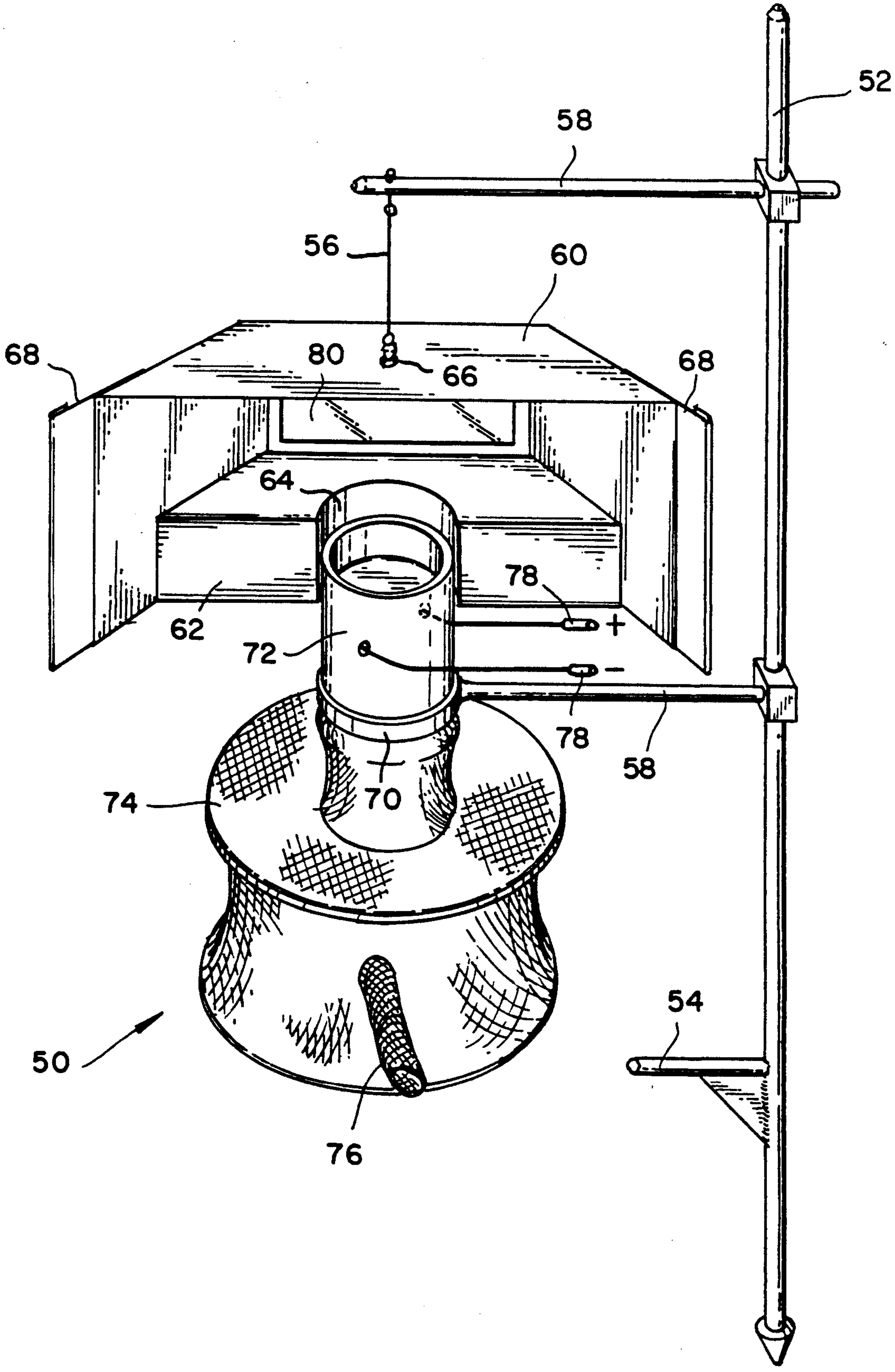
FIG. 2 is a perspective diagram of a "CDC" (Communicable Disease Center) trap useful in carrying out the data measurements for determination of the data set forth in the bar graph of FIG. 1.

FIG. 2 is a perspective diagram of a "CDC" (Communicable Disease Center) trap useful in carrying out the data measurements for the determination of the data set forth in the bar graph of FIG. 1. This trap has the following components:

Support leg (52), foot piece (54), cross arms (58), cover (60), recessed shelf (62), recessed shelf portion (64), suspension bar (56), balancing panels (68), clamps (70), metal cylinder holding fan and motor (72), screen cage (74), aspirating sleeve (76), electric terminals of motor (78) and plastic window (80).

The single support (52), a 4 foot length of ½" outside diameter pipe, is fitted with a foot piece (54), braced at right angles 10 inches from the lower sharpened end of the pipe. Two cross arms (58) clamped to the support are adjustable for height and length. From the upper cross arm, a cover (60), which rotates with the wind, is suspended. This cover, 0.040-gauge aluminum, is a horizontally oriented trapezoid 17.5 inches across the open front, 7.75 inches across the back, and 5 inches deep, with a height of 6 inches. A recessed shelf, (62), 2.75 inches wide, connects at the back of the cover at a height of 2.25 inches. A 4-inch diameter semicircular notch (64), is recessed in the center of the forward edge of the shelf; and the front edge of the shelf, including the semicircular portion, is extended vertically downward for a distance of 2.25 inches, making the edge flush with the back and sides of the cover. The back portion of the aluminum cover above the shelf contains a transparent plastic window(7.75×3.75 inches) (80). The cover parts are fastened togehter with pop rivets, and a hole (66) in the top is centered over the front edge of the semicircular recessed portion in the shelf. Adjustable sliding panels (68) provide additional weight on the front edge so that the cover will balance when suspended by a wire through the centered hole (66) in the top.

A galvanized metal cylinder (72), 6 inches high and 3.5 inches in diameter, is attached to the end of the lower cross arm by a hose clamp (70). This cylinder (72) houses a 4.5 direct current motor which drives a two-bladed 3.125 inch fan located 1.5 inches above the lower end of the cylinder. A collapsible cylindrical cage 10 inches in diameter and 6 inches high (74) equipped with a sleeve 1 inch in diameter (76) for aspirating male and female Mediterranean sand flies (*Phlebotomus papatasi*), is attached to the lower end of the cylinder by an elastic sleeve.

The color pattern of the trap is as follows: the supports and the exposed metal portion, both outside and inside of the top, back, and sides of the cover, are gloss white; the shelf including the vertical front portion is gloss black; the outside of the cylinder and the upper half of the inside are gloss black.

A 6-volt battery, painted white to minimize its attractant qualities for the male and female Mediterranean sand flies (*Phlebotomus papatasi*) provides energy for the trap. Electrical connections (78) to the motor are made by wiring which fits into slots in the cylinder.

In the field the support is driven into the ground and the lower cross arm is adjusted so that the cage (74) is off the ground and the cylinder (72) is sufficiently away from the support to allow the cover to rotate. The upper cross arm is then adjusted so that the semicircular recessed area of the shelf is centered on the cylinder with the shelf about 0.5 inches above the upper edge of the cylinder. The position of the cover is checked to insure free rotation about the stationary cylinder (72). The apparatus of FIG. 1 is described in detail in Mosquito News, Volume 30, No. 1, Article entitled "A Modified Visual Trap For *Aedes Aegypti*" by Richard W. Fay and William H. Prince (From the Biology Section, Technical Development Laboratories, Laboratory Division, National Communicable Disease Center, Health Services and Mental Health Administration, Public Health Service, U.S. Department of Health, Education, and Welfare, Savannah, Ga. 31402).

The entire "CDC" trap apparatus is given the reference numeral 50.

Figure 3:
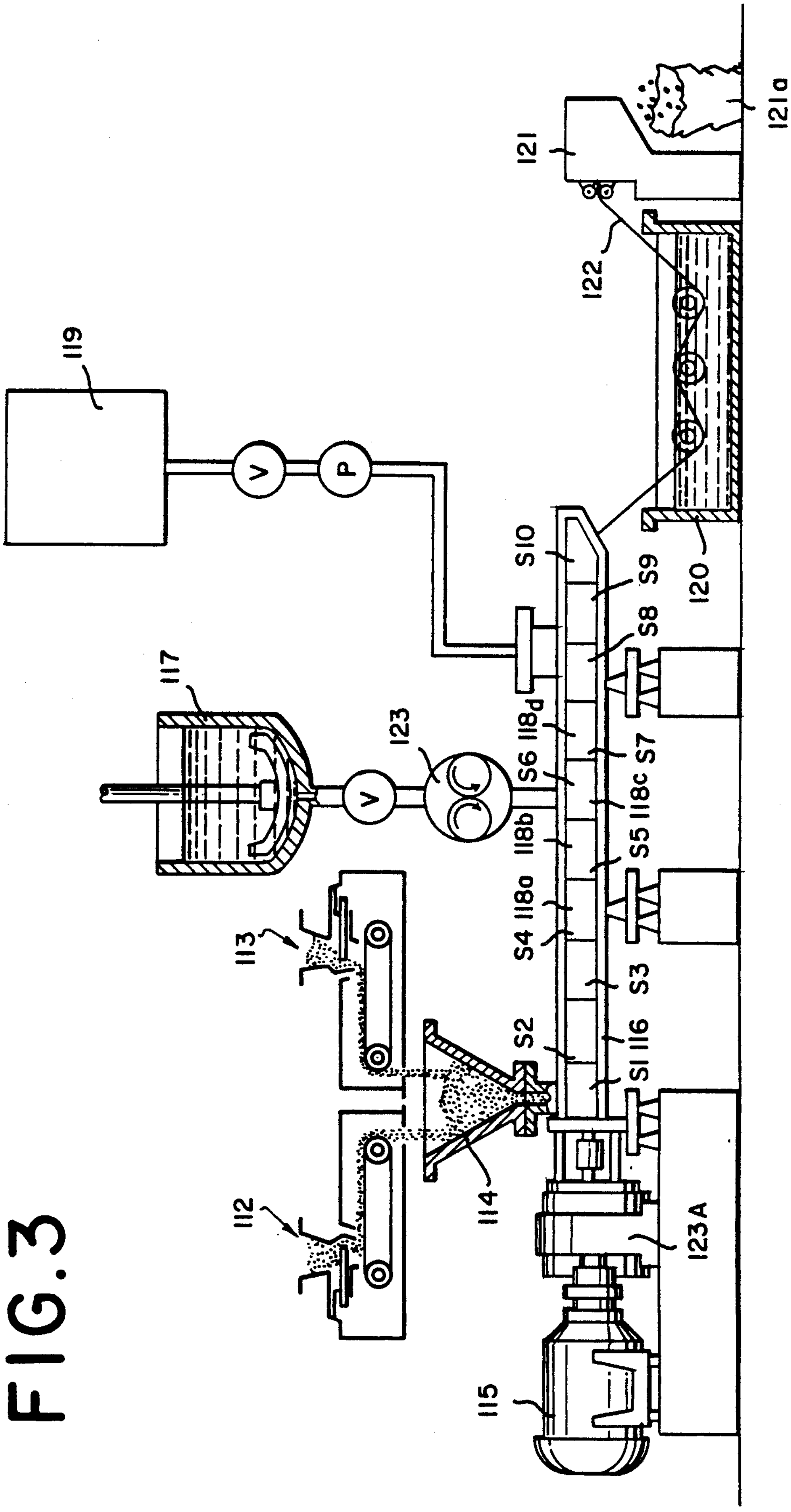
FIG. 3 is a cut-away side elevation schematic diagram of a screw extruder during the compounding of a resin with the insect attractant (alpha-terpineol, dibutyl succinate or combination thereof) while simultaneously adding foaming agent into the hollow portion of the barrel of the extruder and incorporates the pelletizing apparatus used in pelletizing the extruded foamed tow produced as a result of the extrusion operation.

FIG. 3 is a schematic cut-away elevation diagram of an extrusion and pelletizing apparatus useful in carrying out a process of our invention during the operation of said apparatus whereby the female Mediterranean sand fly (*Phlebotomus papatasi*) attractant is incorporated into a polymer such as polyethylene. Motor 115 drives the extruder screws located at 123A in barrel 116, the extruder being operated at temperatures in the range of from about 150° C. up to about 250° C. At the beginning of the barrel, resin at source 112 together with additives, e.g., processing aids and densifiers at location 113 is added via addition funnel 114 into the extruder. Si multaneously (when the operation reaches "steady state"), female Mediterranean sand fly (*Phlebotomus papatasi*) attractant, alpha-terpineol, dibutyl succinate or a mixture of alpha-terpineol and dibutyl succinate is added to the extruder at one, two or more of barrel segments S-3, S-4, S-5, S-6, S-7 and S-8 of the extruder (which may be a twin screw or single screw extruder) at locations 118*a*, 118*b*, 118*c* and 118*d* (for example) by means of gear pump 123 from source 117. From source 119 into barrel segments S-5, S-6, S-7, S-8, S-9 and S-10, a gaseous or liquid blowing agent, e.g., nitrogen, carbon dioxide and the like as described, supra, are added simultaneously with the addition of the female Mediterranean sand fly (*Phlebotomus papatasi*) attractant, e.g., alpha-terpineol, dibutyl succinate or a combination of alpha-terpineol and dibutyl succinate The feed rate range of resin is about 80–300 pounds per hour. The feed rate range of the female Mediterranean sand fly (*Phlebotomus papatasi*) attractant is between 1 and 35% of the feed rate range of the resin. The blowing agent rate range is such that the pressure of the gas or the pressure over the liquid being fed into the extruder is between about 50 and 200 psig if, indeed, blowing agent is added. If desired, the extruded ribbon or cylinder may be passed through a water bath 120 and pelletizer 121 into collection apparatus 121*a*.

What is claimed is:

1. A method of attracting female Mediterranean sand flies (*Phelbotomus papatasi*) to an insect trap comprising the step of exposing the environment surrounding said trap to an insect attractant-containing polymer which consists of a mixture of a polymer and from about 1% up to about 45% by weight of the polymer of dibutyl succinate, said polymer being compatible with said dibutyl succinate.

* * * * *